(12) United States Patent
Nihtilä

(10) Patent No.: US 6,817,979 B2
(45) Date of Patent: Nov. 16, 2004

(54) SYSTEM AND METHOD FOR INTERACTING WITH A USER'S VIRTUAL PHYSIOLOGICAL MODEL VIA A MOBILE TERMINAL

(75) Inventor: Jukka Nihtilä, Espoo (FI)

(73) Assignee: Nokia Corporation, Espoo (FI)

( * ) Notice: Subject to any disclaimer, the term of this patent is extended or adjusted under 35 U.S.C. 154(b) by 197 days.

(21) Appl. No.: 10/185,899

(22) Filed: Jun. 28, 2002

(65) Prior Publication Data

US 2004/0002634 A1 Jan. 1, 2004

(51) Int. Cl.[7] .............................. A61B 5/00; G09G 5/00
(52) U.S. Cl. ...................... 600/300; 128/903; 128/920; 128/897; 345/706
(58) Field of Search .............................. 600/300–301; 128/897, 903–905, 920–925; 705/1–4, 10; 482/8–9; 434/262, 235–238; 455/474; 379/106.1; 345/706; 73/379.01; 700/130, 67; 348/143; 702/19

(56) References Cited

U.S. PATENT DOCUMENTS

| | | |
|---|---|---|
| 5,553,864 A | 9/1996 | Sitrick |
| 5,572,646 A | 11/1996 | Kawai et al. |
| 5,736,982 A | 4/1998 | Suzuki et al. |
| 5,911,129 A | 6/1999 | Towell |
| 5,966,526 A | 10/1999 | Yokoi |
| 6,091,410 A | 7/2000 | Lection et al. |
| 6,167,362 A * | 12/2000 | Brown et al. ............... 434/262 |
| 6,213,871 B1 | 4/2001 | Yokoi |
| 6,227,966 B1 | 5/2001 | Yokoi |
| 6,268,872 B1 | 7/2001 | Matsuda et al. |
| 6,397,080 B1 | 5/2002 | Viktorsson et al. |
| 6,545,682 B1 * | 4/2003 | Ventrella et al. ............ 345/473 |
| 6,665,577 B2 * | 12/2003 | Onyshkevych et al. ..... 700/130 |

FOREIGN PATENT DOCUMENTS

| | | |
|---|---|---|
| EP | 0 807 902 A2 | 11/1997 |
| EP | 0843 168 | 5/1998 |
| JP | 2001016563 | 4/1999 |
| WO | WO009828908 A1 * | 2/1998 |
| WO | WO 98/28908 | 7/1998 |
| WO | WO 98/57474 | 12/1998 |

* cited by examiner

*Primary Examiner*—Charles Marmor
*Assistant Examiner*—Michael Astorino (57) ABSTRACT

A system and method provide for interacting with a virtual physiological model of a user with use of a mobile communication device. Physiological data associated with the user is acquired from the user. The physiological data is transmitted to the mobile communication device, preferably with use of a wireless communication protocol. The methodology further involves using the mobile communication device to communicate the physiological data to a network server. The physiological data is integrated into the virtual physiological model of the user. The user can access data and depictions of the user developed from the physiological data.

46 Claims, 7 Drawing Sheets

SYSTEM AND METHOD FOR INTERACTING WITH A USER'S VIRTUAL PHYSIOLOGICAL MODEL VIA A MOBILE TERMINAL

FIELD OF THE INVENTION

The present invention relates generally to communication of user information via a mobile terminal and, more particularly, to systems and methods for interacting with a physiological model created for a user via a physiological sensor device and a mobile terminal.

BACKGROUND OF THE INVENTION

Good physical fitness is key to maintaining good health and fighting disease. Medical evidence has shown that excess body fat, for example, poses a major threat to health and longevity. Excess body fat is linked to major physical threats, such as heart disease, cancer, and diabetes. Consistent exercise is an important factor in maintaining proper weight and good health.

Motivation plays a significant role in one's interest in continuous and productive exercise. Although exercise videos, programming, and literature abound, many people quickly lose interest in such short-term motivational tools. Such conventional exercise enhancements generally fail to provide the requisite feedback needed to keep an individual motivated in a given exercise regimen.

The inability to provide real-life information concerning fitness training that associates exercise to physical fitness results in an easily perceivable manner limits the usefulness of conventional exercise motivational techniques over the long term.

As contemporary lifestyles have become increasingly fast-paced and complicated, the number of personal electronic devices carried on the person has increased. It is not uncommon for an individual to carry a cellular phone, a PDA, some form of calculator, a pager, and a portable personal medical device, such as a body fat measuring device, heart rate monitor or pedometer, for example. The inconvenience of physically transporting and accounting for such devices often results in eliminating certain devices from one's personal inventory of devices. In many cases, personal medical devices, such as heart rate monitoring devices, which can enhance exercise regimens and provide motivation for healthier lifestyle habits, are cast aside in favor of more utilitarian devices, such as the now ubiquitous cellular phone.

There is a need for integration of mobile communications and health promoting devices, such as heart rate monitoring devices. There is a need for improved motivational techniques that allow individuals to associate real-life physiological data with the individual's progress toward particular fitness goals. The present invention addresses these and other needs, and provides additional features and advantages over conventional implementations and techniques.

SUMMARY OF THE INVENTION

The present invention is directed to a system and method of interacting with a virtual physiological model of a user with use of a mobile communication device. According to one methodology of the present invention, physiological data associated with the user is acquired from the user. The physiological data is transmitted to the mobile communication device, preferably with use of a wireless communication protocol. The methodology further involves using the mobile communication device to communicate the physiological data to a network server. The physiological data is integrated into a virtual physiological model of the user.

The acquired physiological data can include one or more of the user's weight, caloric consumption, blood pressure of the user, information concerning the user's diet, and anatomical measurements of the user, for example. A number of physical characteristics of the user can be developed using the physiological data of the virtual physiological model. Such physical characteristics of the user can include one or more of muscle mass, percent body fat, anatomical dimensions, energy consumption, stress level, heart rate characteristics, and rate of recovery from an exercise regimen, for example.

In accordance with another embodiment, a method of interacting with a virtual physiological model of a user involves acquiring physiological data associated with the user and transmitting the physiological data to a network server using the mobile communication device. The physiological data is integrated into the virtual physiological model of the user. Fitness data is generated using physiological data associated with the virtual physiological model of the user. The fitness data is communicated to the user.

The fitness data can include heart rate data associated with a specified period of time, a rate at which the user recovers from an exercise regimen, a mapping of heart rate data to each of a number of physiological data states or user depictions developed from the virtual physiological model. The fitness data can also include stress level data associated with the user and one or both of percent body fat data and muscle mass of the user.

Communicating fitness data to the user can involve communicating a depiction of the user based on the physiological data associated with the virtual physiological model of the user. Changes to the user's depiction can be effected in response to changes to the physiological data associated with the virtual physiological model of the user. For example, changes to one or more anatomical dimensions of the user can be depicted. The depiction of the user can include one or both of graphical and textual information based on the physiological data associated with the virtual physiological model of the user.

Historical physiological data of the virtual physiological model can be analyzed to predict changes in the fitness data over time. For example, historical physiological data of the virtual physiological model can be analyzed to predict changes in the fitness data in response to a set of input data applied to the virtual physiological model of the user. The set of input data can include a set of current physiological data acquired from the user or a set of test physiological data input by the user.

According to another embodiment of the present invention, a mobile physiological information system includes a mobile communication device and a physiological sensor device adapted for acquiring physiological data associated with the user. The system further includes a transfer device communicatively coupled to the physiological sensor device and the mobile communication device. The transfer device transmits the physiological data to the mobile communication device for subsequent integration into a virtual physiological model of the user.

In accordance with another embodiment of the present invention, a mobile physiological information system communicates with a network and a network server. The system includes a fitness data engine operable at the network server, a mobile communication device, and a physiological sensor device adapted for acquiring physiological data associated with the user. The system further includes a transfer device communicatively coupled to the physiological sensor device and the mobile communication device. The transfer device transmits the physiological data to the mobile communication device, and the mobile communication device communicates the physiological data to the fitness data engine. The fitness data engine integrates the physiological data into a virtual physiological model of the user and generates fitness data using physiological data associated with the virtual physiological model of the user for subsequent transmission to the user.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail. It is to be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF VARIOUS EMBODIMENTS

In the following description of the illustrated embodiments, reference is made to the accompanying drawings which form a part hereof, and in which is shown by way of illustration, various embodiments in which the invention may be practiced. It is to be understood that the embodiments may be utilized and structural changes may be made without departing from the scope of the present invention.

The present invention is directed to systems and methods for using mobile communication techniques to enhance an understanding of the physiological state of an individual based on physiological information acquired from the individual in real-time. The principles of the present invention find particular applicability in the context of development, refinement, and monitoring of physical fitness regimens and training, and verification of the effectiveness of such regimens and training over time.

Systems and methods of the present invention provide for the generation of, and maintenance and modification to, a virtual physiological model, referred to herein as an avatar, of an individual. The virtual physiological model, in general, characterizes the physiological state of an individual based on physical statistics of the individual (e.g., weight, height, gender, and age) and physiological data acquired from the user in real-time.

Employment of a visual depiction or characterization of a user's real-time physiological state in accordance with the principles of the present invention provides a comprehensive visual physical fitness feedback methodology heretofore unavailable using conventional physiological monitoring techniques.

The integration of multiple sources of real-life physiological data for a given user enables a much more accurate characterization, and, therefore, understanding, of the user's state of physical fitness in real-time and the effects of various training regimens undertaken by the user.

As such, exercise and training regimens can be developed and augmented over time to facilitate achievement of particular physical fitness goals of a given user. The accuracy by which the impact of fitness training of a user is measured can be significantly improved by employment of the systems and method of the present invention. Further, by presenting the impact of fitness training in the form of an avatar, which provides a unique, entertaining, and real-life characterization of the user's physical state of being, a user is motivated to remain committed to improved physical fitness.

Physiological data is preferably acquired from the user through use of non-invasive techniques. Various types of physiological data can be acquired from the user, including, in particular, heart rate data. Blood pressure data can be acquired from time to time and incorporated into the virtual physiological model of the user. Body temperature, particularly when measured during extended periods of exertion, can also be acquired. Oxygen saturation and oxygen consumption can also be measured and incorporated into the user's virtual physiological model. Further, percent body fat can be determined and incorporated into the user's virtual physiological model. Various other physiological parameters can be acquired or developed for incorporation into the user's avatar.

In addition, the virtual physiological model of the user incorporates various information about the user's stature, age, gender, weight, anatomical dimensions, and diet. For example the model can incorporate the dimensions of the various parts of the user's anatomy, such as waist, arms, legs, torso, and neck dimensions, for example. The diet of the user, which can include a percentage and caloric consumption of fats and carbohydrates, for example, can be incorporated as data associated with the avatar.

Physiological data is preferably acquired in real-time throughout each day.

The rate of sampling or recording of a user's physiological data can be constant or, more preferably, varied depending on a number of factors, such as time of day and activity level of the user. For example, the rate, amount, and/or variety of physiological data acquired from the user preferably increases during periods of increased activity, such as during exercise, training, and periods of elevated stress, and decreases during periods of decreased activity, such as during sleep.

The acquired physiological data is used to generate various types of fitness data. In one form, the fitness data can include various types of physiological parameters, and changes to such parameters over time, computed using the user's acquired physiological data, such as average heart rate during exercise, recovery rates from exertion, stress level, caloric consumption, muscle mass, percent body fat, and oxygen consumption during exertion. In another form, the fitness data can include graphical or animation data, in which physical attributes of the user are visually depicted in the form of an avatar. Changes to the avatar can be effected in response to changes in the user's acquired physiological data over time, to predictions based on historical physiological data, and to predictions based on test physiological data and/or training regimen parameters.

By way of example, a user can create an avatar representative of the current physical state of the user. The user can adjust the avatar to change the appearance of the avatar to a more desired appearance. For example, the anatomical dimensions of the avatar can be changed to reflect desired waist, chest, upper arms, and thigh dimensions, for example. Given differences between the desired avatar features and present avatar features, various training, diet, and related fitness recommendations can be developed to establish a training regimen(s) most suited to helping the user achieve the desired fitness goals. Physiological data is subsequently acquired and applied to the user's avatar, and compared to the desired avatar's data, to determine if the training regimen is effective in achieving the desired fitness goals. Further alterations in the training regimen and/or diet can be made, the effects of which can be monitored by subsequent acquisition of the user's physiological data.

Figure 1:
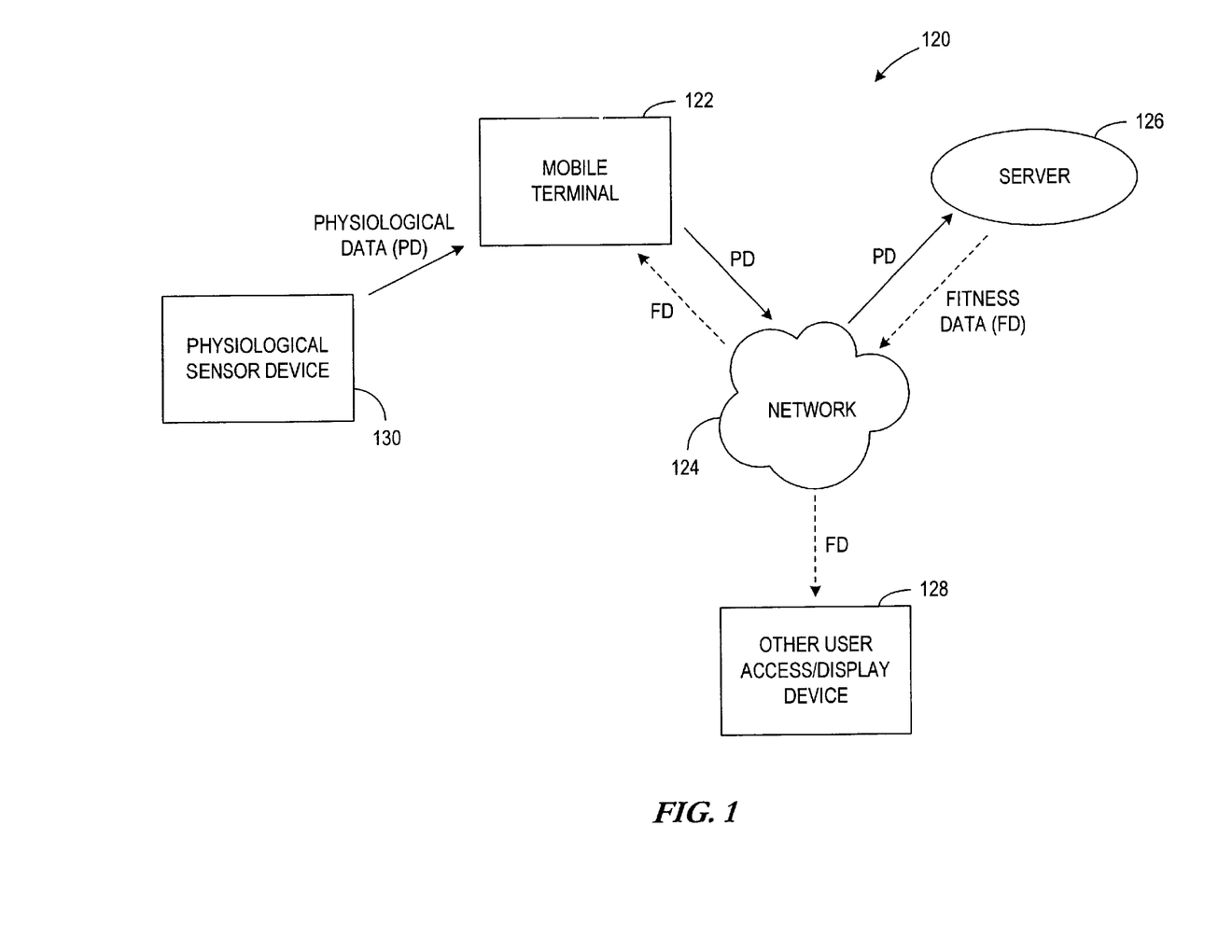
FIG. 1 illustrates a system for acquiring physiological data from a user and communicating the physiological data via a mobile terminal to a network server for integration into a virtual physiological model established for the user in accordance with an embodiment of the present invention.

Turning now to the drawings, and more particularly to FIG. 1, there is illustrated a system 120 for acquiring physiological data from a user and communicating the physiological data via a mobile terminal to a network server for integration into a virtual physiological model established for the user in accordance with an embodiment of the present invention. FIG. 1 shows a physiological sensor device 130 communicatively coupled to a mobile terminal 122. The physiological sensor device 130 is intended to represent one or more sensing devices that sense one or more physiological parameters of a user, such as heart rate, for example. The physiological sensor device 130 is communicatively coupled to mobile terminal 122 via a wireless link, such as wireless link that conforms to the Bluetooth wireless specification. In another configuration, the physiological sensor device 130 can be coupled to the mobile terminal 122 via a hard wired connection, although it is perceived that a wireless link is more desirable in most cases.

The physiological sensor device 130 acquires physiological data (PD) from the user and transmits this data to the mobile terminal 122. According to one approach, the mobile terminal 122 effectively functions as a modem by communicating the physiological data received from the physiological sensor device 130 to a radio network 124, such as a 2G or 3G network. It is noted that the network 124 shown in the figures can alternatively be representative of an IP or Mobil IP network, such as an IPv4, IPv6, or hybrid IPv4/IPv6 network for example.

According to another approach, the mobile terminal 122 cooperates with the physiological sensor device 130 to buffer physiological data received from the physiological sensor device 130, noting that portions of the physiological data acquired by the physiological sensor device 130 in real-time can be stored/buffered in memory of one or both of the mobile terminal 122 and physiological sensor device 130. This cooperative use of distributed memory is of particular use when significant amounts of real-time physiological data obtained by several sensors are acquired, and in situations where a communication link between the mobile terminal 122 and network 124 cannot be established or is unstable/unreliable.

The physiological data communicated from the mobile terminal 122 to the network 124 is routed to a server 126 which is configured to accept and process this data. The server 126 stores and executes processing software that, in general, operates on the physiological data received from each of a number of users. The processing software integrates currently or recently acquired physiological data into the user's virtual physiological model (i.e., avatar). The user can review the data associated with his or her avatar using the mobile terminal 122 or other user access/display device 128.

The server 126 also provides for the creation of a user-specific avatar by each of a number of users, and further provides for interaction between users and their respective avatars. It can be appreciated that the information associated with a user's avatar is highly personal in nature. As such, access to a user's avatar and information associated with the avatar is typically subject to tight access restrictions. For example, access rights to a user's avatar and related information are typically granted only to the user, who can typically grant access rights at various security levels to others as desired.

The processing software further computes fitness data (FD) of various types, including, textual, graphical, animation, audio, video, or other form of fitness data. As previously discussed, the fitness data can include various types of physiological parameters, changes to such parameters over time, training and diet recommendations, and various views of the user's avatar, among other forms of data. The fitness data is communicated from the server 126 to the user via the network 124. The fitness data can be communicated to the mobile terminal 122 or some other user access/display device 128.

According to one implementation, the mobile terminal 122 can receive the fitness data in the form of a training regime and upload this fitness data to the physiological sensor device 130. The training regimen, according to this illustrative example, can include a sequence of programmable heart rate range limits and durations associated with a given exercise routine. The programmed sequence can provide upper and lower heart rate limits for each period defining the routine, in which an alarm is activated if the user's recommended heart rate falls outside of an applicable heart rate range for a given exercise period. In another implementation, it may be desirable to view the user's avatar on a display coupled to the physiological sensor device 130, rather than on the display of the mobile terminal 122. This may be the case where the subject physiological sensor device 130 is implemented as a table-top system, rather than a portable or ambulatory device.

Figure 2A:
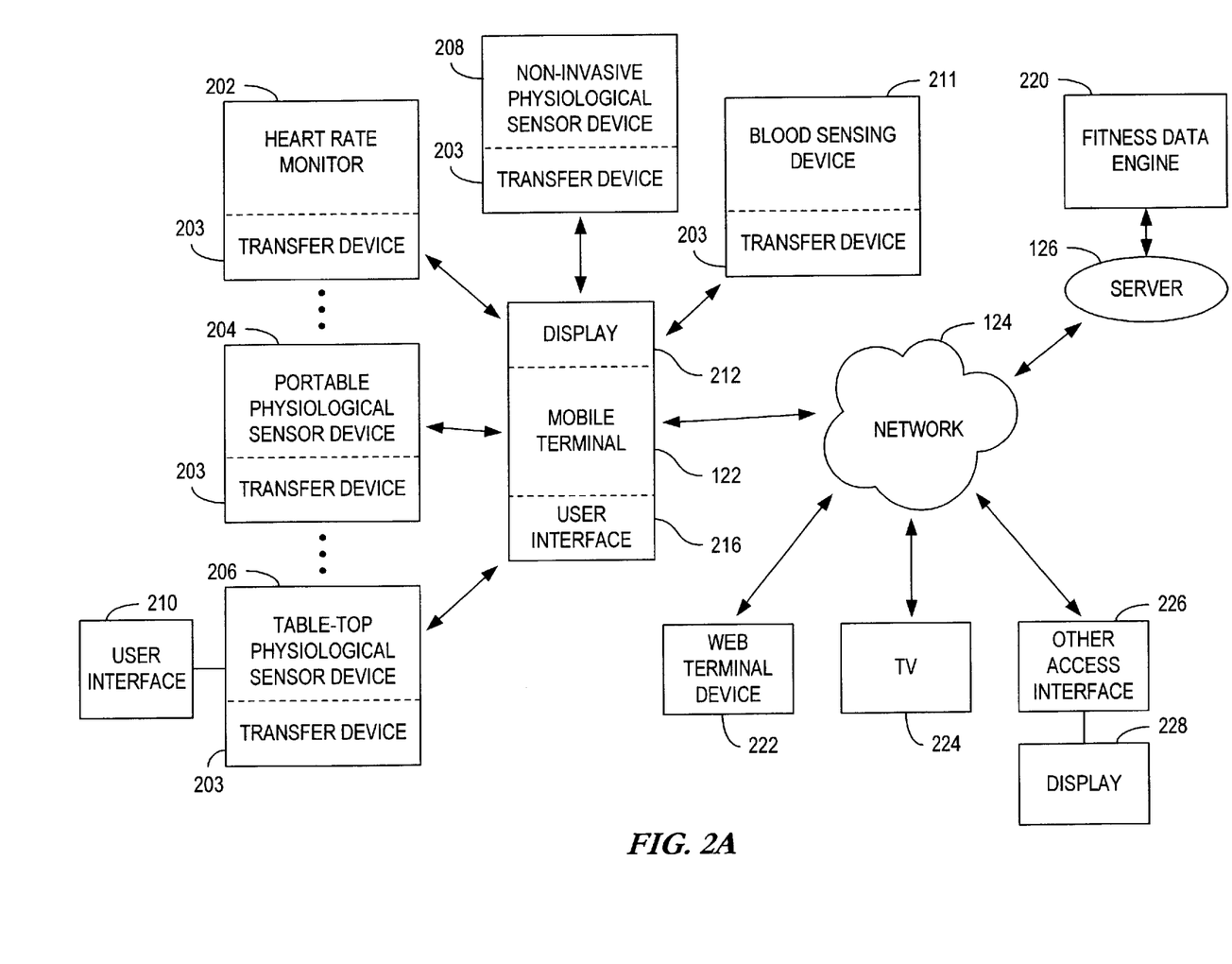
FIG. 2A is a depiction of a system for acquiring physiological data from a user and communicating the physiological data via a mobile terminal to a network server for integration into a virtual physiological model established for the user in accordance with another embodiment of the present invention.

FIG. 2A is a depiction of a system for acquiring physiological data from a user and communicating the physiological data via a mobile terminal to a network server for integration into a virtual physiological model established for the user in accordance with another embodiment of the present invention. According to this embodiment, a number of different physiological sensor devices can be employed to acquire a variety of different physiological parameters from a user. As shown in the illustrative embodiment of FIG. 2A, a system of the present invention can include a variety of physiological sensor devices, including portable or ambulatory sensor devices, table-top or stationary sensor devices, and a combination of these devices. The physiological sensor devices are preferably non-invasive devices. It is understood that a system of the present invention can range in sophistication from simple configurations, in which one or perhaps two physiological sensor devices are employed, to complex configurations, in which several physiological sensor devices are employed.

Each of the physiological sensor devices includes an integral transfer device 203 which facilitates the transmission of acquired physiological data to a mobile terminal 122. According to this embodiment, the transfer device 203 includes a communication device configured to operate in conformance with the Bluetooth wireless specification. The mobile terminal 122 also has the capability to communicate with the transfer device 203 in conformance with the Bluetooth wireless specification. The transfer device 203 can be configured to provide for uni-directional or bi-directional communication with the mobile terminal 122.

As discussed previously, physiological data, such as heart rate data, can be acquired and transmitted to the mobile terminal 122 via the transfer device 203 in real-time. Alternatively, physiological data can be buffered in memory of one or both of the physiological sensor device and mobile terminal 122. In a real-time mode of operation, the mobile terminal 122 operates effectively as a modem to facilitated the transfer of acquired physiological data between the physiological sensor device, mobile terminal 122, network 124, and server 126 in real-time.

A fitness data engine 220 supported by the server 126 can receive the acquired physiological data in real-time, interact with the user's avatar, such as by integrating the acquired physiological data into the avatar, generate fitness data, including various processed data and avatar depictions, and transmit the fitness data to the mobile terminal 122 or other user access/display device in real-time. It is understood that these data can also be transmitted between the various communication elements on a non real-time basis.

The mobile terminal 122 includes a display 212 and user interface 216, among other standard components. The user interface 216 of the mobile terminal 122 can be used to input various types of user related information needed to create, modify, or otherwise interact with the user's avatar residing on the server 126. For example, the user can input weight, height, age, gender, and other physical and personal information to the user's virtual physiological model via the mobile terminal's user interface 216. Alternative or in addition, this information can be input using a user interface of a given physiological sensor device that provides such an interface.

Various commands to access and interact with the user's virtual physiological model can be generated using the user interface 216 of the mobile terminal 122. Various types of textual, graphical, audio, motion video, and animation data received from the fitness data engine 220 and server 126 can be displayed on the display 212 of the mobile terminal 122, which also includes a speaker. In addition, these various data types can be transmitted from the server 126/fitness data engine 220 to a user by use of a WEB terminal device 222, television 224, or other access interface 226 that employs a display 228.

As is shown in the embodiment of FIG. 2A, a physiological data acquisition system of the present invention preferably includes at least a heart rate monitor 202. The heart rate monitor 202 is preferably implemented as a personal non-invasive heart rate measuring device. The heart rate monitor 202, for example, can be implemented as a two-part device comprising a belt-type heart rate transmitter containing EKG electrodes and a wristband-type receiver unit in telemetric inductive or optical connection with the transmitter. The receiver unit generally includes a microprocessor, memory, a display, and a user interface.

In an alternative arrangement, the heart rate monitor 202 can be entirely integrated into a wristband, whereby a sensor, such as EKG electrodes or a pressure sensor, is also arranged in the wristband. Alternatively, all of the components can be integrated into a heart-rate-measuring belt. The rate sensor can further be implemented as an optical sensor that measures the user's heart rate. Other configurations of a heart rate monitor 202 as are known in the art may be employed.

The user's heart rate can be acquired according to a monitoring program stored in memory of the heart rate monitor 202. Heart rate data can, for example, be acquired on a continuous basis, a variable basis, on command by the user, on the basis of the user's activity level or in response to a remote command signal received from by the heart rate monitor 202 from the network 124 via the mobile terminal 122.

A physiological data acquisition system of the present invention can employ one or more other types of portable or ambulatory physiological sensor devices 204. Such portable physiological sensor devices 204 are typically worn by the user using a wristband, belt, or other harness that provides for user comfort and high mobility. In the case of a heart rate monitor 202, for example, this physiological sensor device is in continuous contact with the user's anatomy during use. In the case of other portable physiological sensor devices 204, such devices can be carried within the user's clothing, pouch or other carrying arrangement, and be brought into contact with the user's anatomy only when the physiological parameter of interest is to be measured.

A physiological data acquisition system of the present invention can include various types of non-invasive physiological sensor devices 208. Such non-invasive physiological sensor devices 208 are typically portable, but need not be in all configurations. A physiological data acquisition system of the present invention can also include various types of table-top physiological sensor devices 206, which are generally not considered highly portable. Such table-top devices 206 can be situated at a location frequented by a user, such as the user's home.

A sphygmomanometer, for example, can be employed as a table-top physiological sensor device 206 that can be used frequently to provide accurate measurement of the user's blood pressure. The table-top physiological sensor device 206, in certain configurations, can include a user interface 210, such as a user input device and display, for example. It is noted that the table-top physiological sensor device 206 or the portable physiological sensor device 204 can employ an invasive approach to sensing a particular physiological parameter of the user.

In accordance with a more complex configuration, a physiological data acquisition system of the present invention can include a blood sensing device 211. The blood sensing device 211 is representative of one or more devices that can be used to measure a number of blood related parameters. Such blood related parameters can include oxygen saturation, oxygen consumption, blood chemistry, and blood pressure, for example.

Figure 2B:
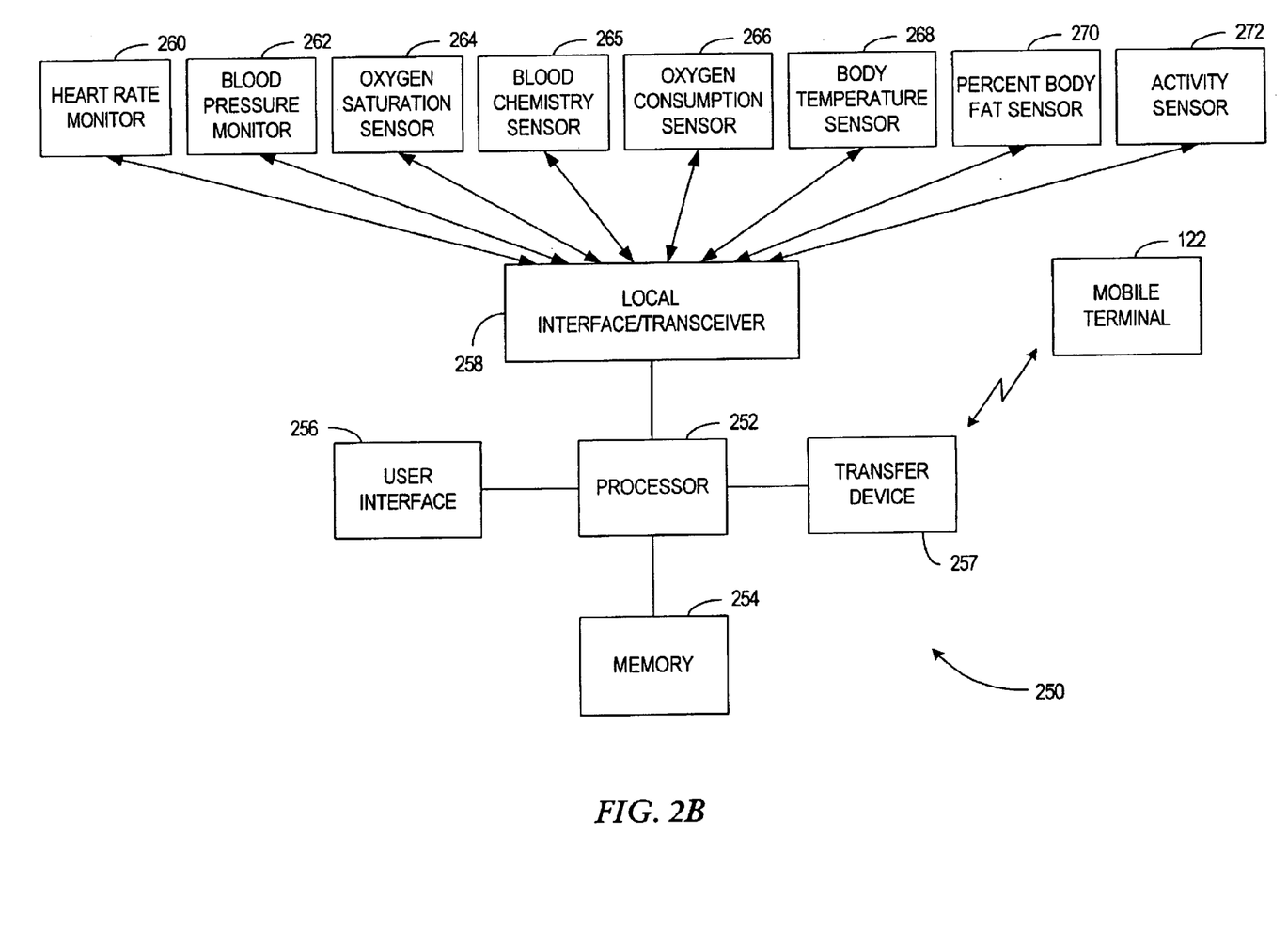
FIG. 2B illustrates a system for acquiring various types of physiological data from a user using a number of different physiological sensor devices.

FIG. 2B illustrates a number of different physiological sensor devices that can be employed in a physiological data acquisition system 250 of the present invention. It is understood that the devices depicted in FIG. 2B do not represent an exhaustive listing of devices that can be employed. Moreover, it is understood that a physiological data acquisition system 250 of the present invention need not incorporate all of the devices shown in FIG. 2B, but can incorporate one or multiple devices.

According to one configuration, the physiological data acquisition system 250 is intended to represent a portable, and preferably wearable, unit that provides for local acquisition of physiological data from one or more physiological sensor devices. The physiological sensor devices may be integral to or separate from the physiological data acquisition system 250. Each of the physiological sensor devices typically communicates with the physiological data acquisition system 250 via an on-board communication device, such as a device that conforms to the Bluetooth wireless specification. The physiological data acquisition system 250 includes a local interface/transceiver 258 that also operates in conformance with the Bluetooth wireless specification. Depending on the type of physiological sensor device employed, a hardwire connection can be established between a given physiological sensor device and the physiological data acquisition system 250 via the local interface/transceiver 258. A user interface 256 and memory 254 are coupled to the processor 252. A transfer device 257, such as a communication device configured to operate in conformance with the Bluetooth wireless specification, is coupled to the processor 252 and provides for unidirectional or bidirectional communication with a mobile terminal 122.

In accordance with another configuration, the processor 252, user interface 256, and memory 254 represent standard components of a mobile terminal. The transceiver device 256, in this configuration, represents standard communication circuitry that provides for communication with a radio network, such as a 2G or 3G network. In this particular case, block 122 would be representative of a network, rather than a mobile terminal as is shown in FIG. 2B. Each of the physiological sensor devices is communicatively coupled to the processor 252 of the mobile terminal via wireless or hardwired connections to the local interface/transceiver 258. Wireless communication between the local interface/transceiver 258 and one or more of the physiological sensor devices is preferably accomplished in accordance with the Bluetooth wireless specification.

As was discussed previously, the physiological data acquisition system 250 preferably includes a heart rate monitor 260 and may further include a blood pressure monitor 262. A body temperature sensor 268 can also be used to monitor changes in the user's body temperature over time, and to develop body temperature profiles for the user during particular exercise regimens. For example, monitoring the body temperature of a marathon runner and developing temperature profiles therefrom can be useful in developing optimal training regimens for such long distance runners.

In a more sophisticated implementation, a physiological data acquisition system 250 of the present invention can include an oxygen saturation sensor 264 which non-invasively measures oxygen saturation of the user's blood. A pulse oximeter, for example, can be used to measure and compute the arterial oxygen saturation level of the user's blood from signals received from the pulse oximeter.

An oxygen consumption sensor device 266 can be employed to measure the user's oxygen consumption. According to one configuration, the oxygen consumption sensor device 266 employs a breathing apparatus which provides oxygen consumption data to a processor of the device 266. The breathing apparatus includes a breathing unit through which the user breathes. In one configuration, an oxygen consumption sensor directly measures the user's oxygen consumption and provides output data indicative of oxygen consumption. A suitable oxygen consumption sensor is commercially available from Medical Graphics Corporation or Beckman Instruments.

In accordance with another configuration, a breathing unit of the oxygen consumption sensor device 266 is coupled to a flow sensor which measures air flow passing through the sensor. Air flow data is transmitted from the flow sensor to the processor of the device 266. In accordance with this configuration, an ambient oxygen sensor is used to determine the content of oxygen in the ambient air, and a second oxygen sensor senses the content of oxygen in the patient's expired air. Alternatively, the content of oxygen in ambient air may be assumed to be 20.93%. The processor of the oxygen consumption sensor device 266 uses the air flow data acquired from the flow sensor, oxygen content data received from second oxygen sensor 67, and assumed (i.e., 20.93%) or sensed oxygen content data (i.e., via the ambient oxygen sensor) to compute oxygen consumption of the user in real-time.

According to a more sophisticated implementation, a physiological data acquisition system of the present invention can include a blood chemistry sensor device 265 which enables various non-invasive blood chemistry measurements. Such blood chemistry measurements can include measurement of hemacrit, which is a measure of the fractional level of red blood cells in the blood, hemoglobin, tissue perfusion, and oxygenation. According to one approach, noninvasive blood chemistry measurements are obtained using NIR (near infrared) spectroscopy techniques.

By way of example, a sensor of the blood chemistry sensor device 265 can employ photonic methods based on fluorescence. For example, the blood chemistry sensor device 265 contains a colored dye immobilized in a polymer film. A blue LED excites fluorescence while a photodiode monitors the resulting red emission. Oxygen interferes with the fluorescence. Greater concentrations of oxygen diminish the red fluorescence emission. A suitable non-invasive blood chemistry measurement device is commercially available from PhotoSense LLC.

In yet another implementation, a physiological data acquisition system 250 of the present invention can include a percent body fat sensor 270. The percent body fat sensor 270 typically includes a number of electrodes that contact surfaces of a user's two hands. Monitoring circuitry transmits monitoring signals between a first pair of the electrodes when in contact with the user's hands. In response to transmission of the monitoring signals, the resistance between a second pair of the electrodes in contact with the user's hands is detected. Percent body fat of the user is computed using the detected resistance.

An activity sensor 272 can also be incorporated into a physiological data acquisition system 250 of the present invention. The activity sensor 272 can include an accelerometer, such as a MEMS (Micro-ElectroMechanical Systems) accelerometer. The activity sensor 272 senses changes in the activity level of the user, and can be used for a number of purposes, such as optimizing physiological sensor device sampling durations and rates, for example.

Figure 3:
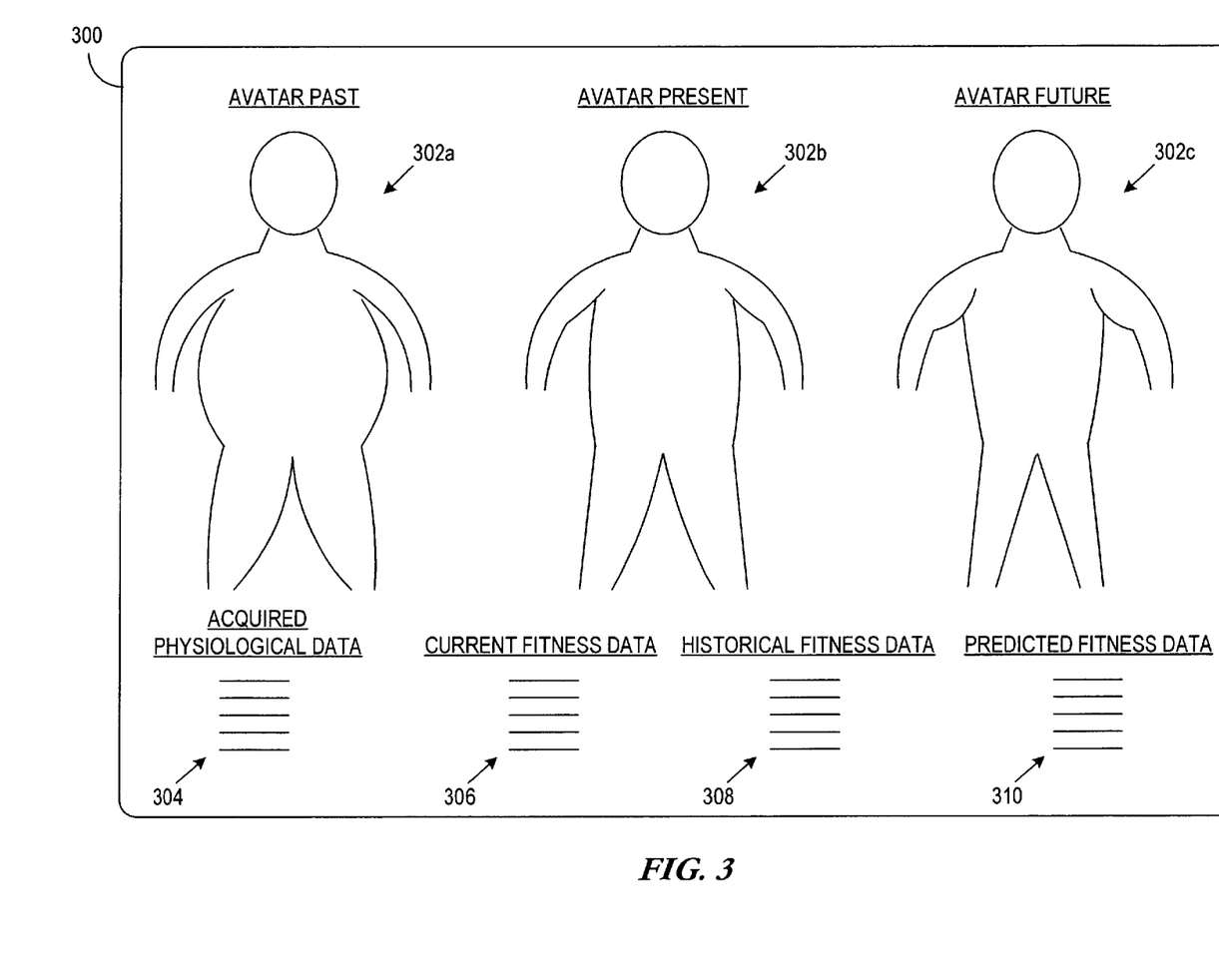
FIG. 3 illustrates a display of graphical and textual fitness related data developed from physiological data acquired from a user, the display showing a visual depiction of the user (i.e., avatar) in various stages of physical fitness in accordance with an embodiment of the present invention.

Turning now to FIG. 3, there is depicted a display 300 on which various types of fitness data within the context of the present invention are displayed. The display 300 represents a display of a mobile terminal, a television, and WEB terminal device, or the display of another access device. Various textual data can be presented, including the data types 304 acquired by the physiological data acquisition system and user input data, such as weight and age, for example. Current fitness data 306 generated by the fitness data engine can be presented on the display 300. Historical fitness data 308 can also be presented on the display 300. Predicted fitness data 310 generated by the fitness data engine can be presented.

A visual representation of the user and user's state of physical fitness can be graphically presented on the display 300. Various physical attributes of the user can be visually depicted in the form of an avatar 302. The present form of the avatar 302b can be displayed, as can a past form 302a based on historical fitness data. Changes to the avatar in response to changes in the user's acquired physiological data over time can be visually depicted. Predictions based on historical physiological data or test physiological data and/or training regimen parameters can be performed to produce data used to develop a future form of the user's avatar 302c. A single avatar or multiple avatars can be selectively presented on the display 300 by the user.

Methods of the present invention can be implemented using the systems and devices described above. In accordance with one particular embodiment, a small number of physiological measurements is acquired from use of a physiological sensor device that requires minimal user intervention, such as a heart rate monitor. By way of example, a pedometer can be employed for calculating energy consumption and heart rate monitoring at a frequency of once a day for thirty seconds while resting. It is understood that the frequency of sampling can be different, but that in this embodiment only a minimal amount of physiological data is needed. Each of the physiological sensing devices directly communicates with the mobile terminal (e.g., via Bluetooth), which relays the information to the network server. The fitness engine on the server calculates the impact of the data on the avatar, and the user can access the updated version of the avatar via one of several access interfaces (e.g., mobile phone, WEB terminal device, TV, etc.). From the perspective of the user's overall experience, it may be desirable to modify the avatar only on a weekly or bi-weekly basis, rather than upon receipt of each set of newly acquired physiological data.

Figure 4:
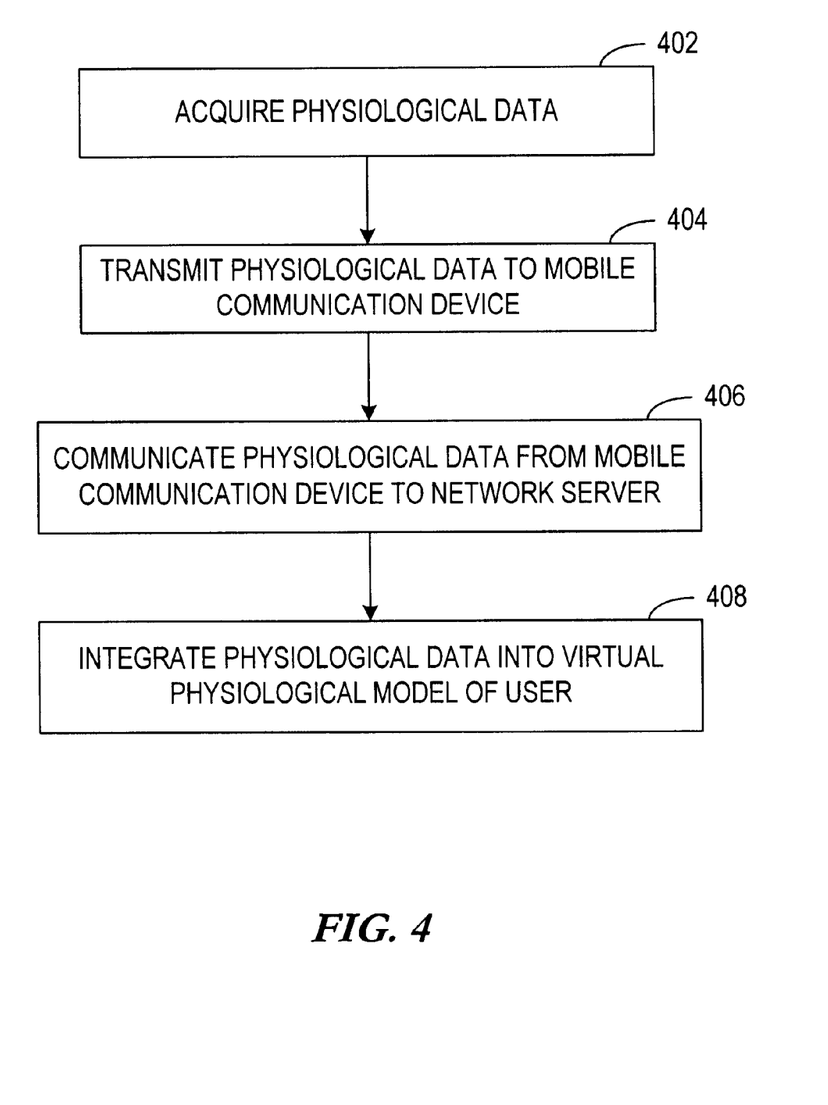
FIG. 4 illustrates a method of acquiring physiological data from a user and communicating the physiological data via a mobile terminal to a network server for integration into a virtual physiological model established for the user in accordance with an embodiment of the present invention.

FIG. 4 illustrates a method of acquiring physiological data from a user and communicating the physiological data via a mobile terminal to a network server for integration into a virtual physiological model established for the user in accordance with an embodiment of the present invention. According to this approach, which is consistent with a general implementation of the present invention, physiological data of various types is acquired 402 from the user. The physiological data is transmitted 404 to a mobile communication device, such as mobile terminal. The physiological data is communicated 406 from the mobile terminal to a network server. The physiological data is integrated 408 into a virtual physiological model of the user, such as an avatar.

Figure 5:
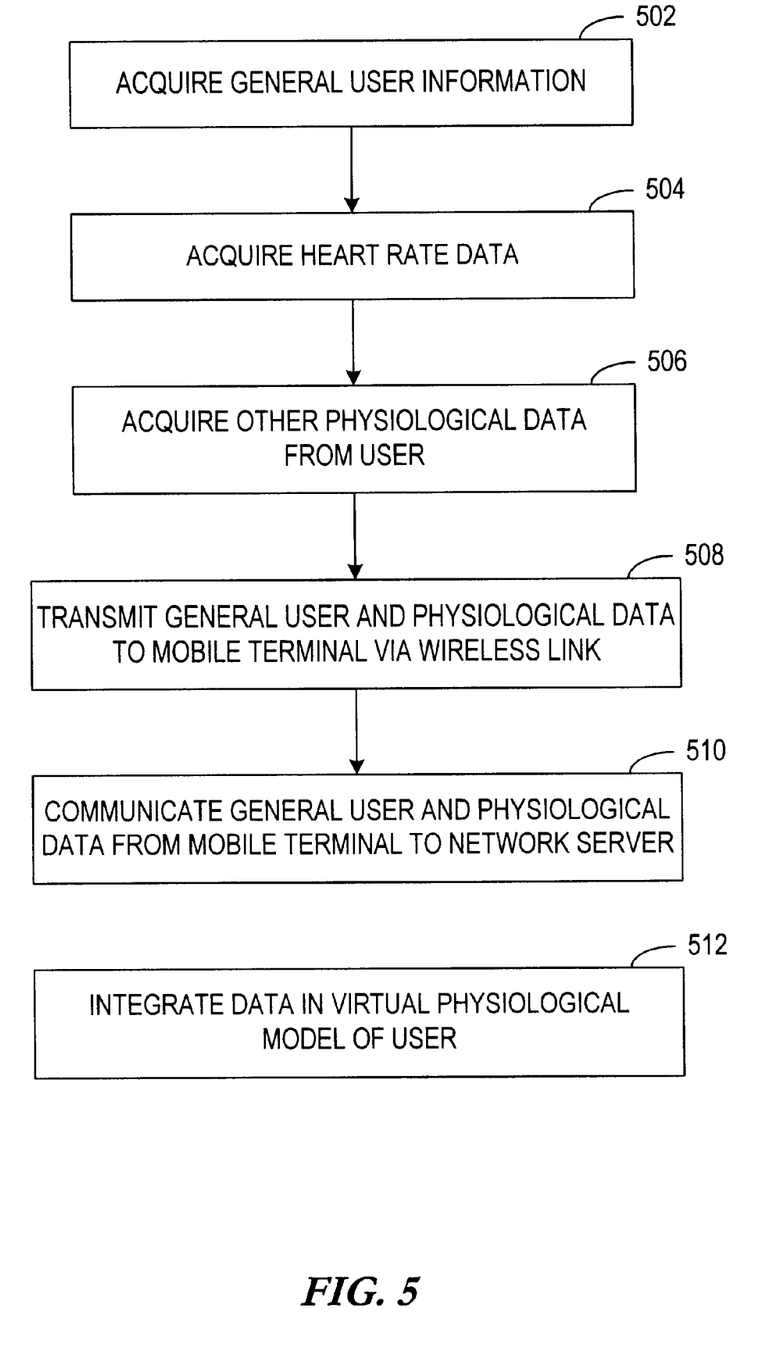
FIG. 5 illustrates a method of acquiring physiological data from a user and communicating the physiological data via a mobile terminal to a network server for integration into a virtual physiological model established for the user in accordance with another embodiment of the present invention.

FIG. 5 illustrates a method of acquiring heart rate data and other data acquired from a user, and communicating this data via a mobile terminal to a network server for integration into a virtual physiological model established for the user in accordance with an embodiment of the present invention. According to this method, general information about the user, such as weight, gender, age, and height, for example, is acquired 502 from the user. Heart rate data is acquired 504 from the user, preferably throughout the day. Other types of physiological data can also be acquired 506. The general and physiological data is transmitted 508 to a mobile terminal via a wireless link and from the mobile terminal to a network server 510. These data are integrated 512 into a virtual physiological model of the user.

Figure 6:
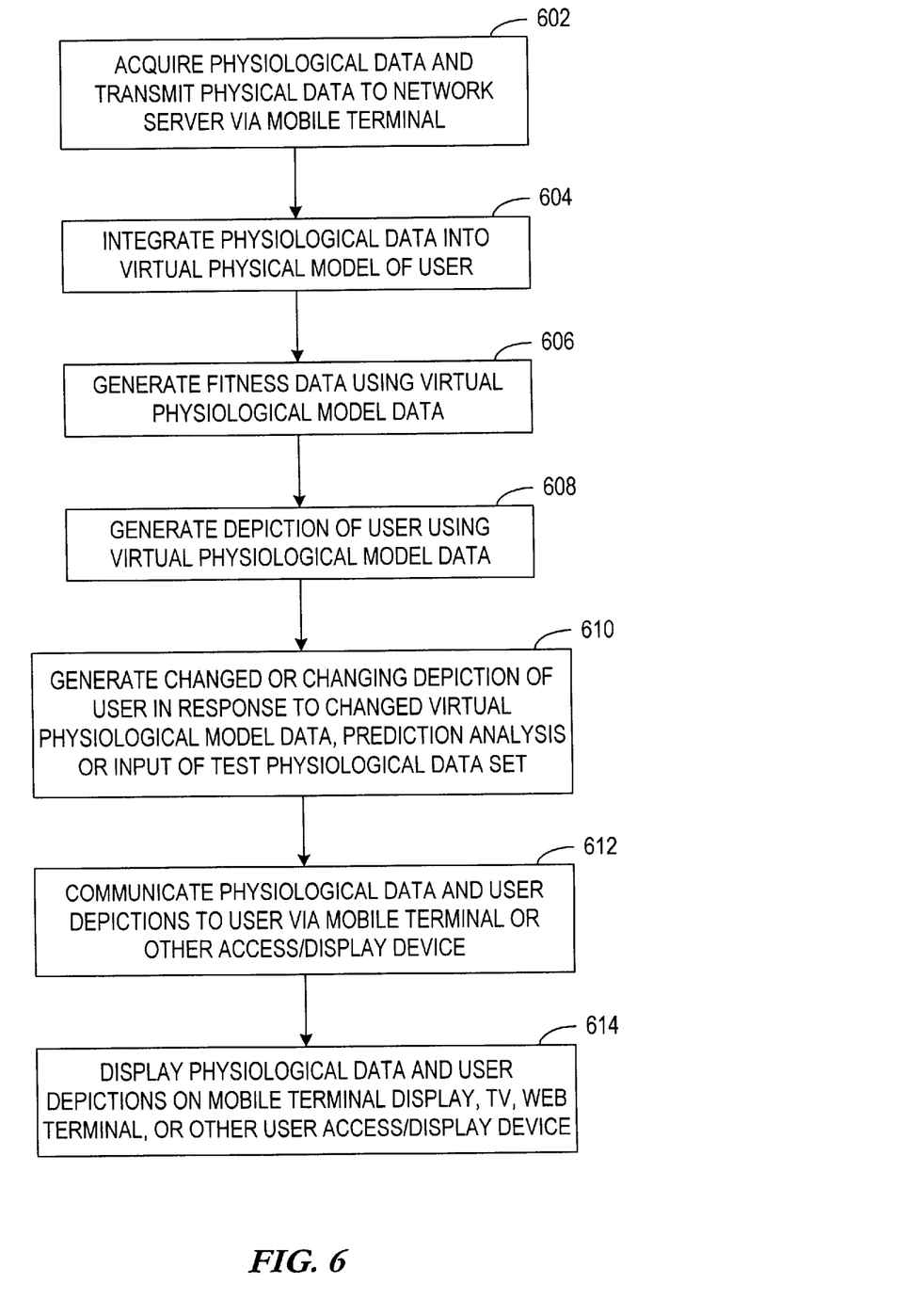
FIG. 6 illustrates a method of generating fitness data and a visual depiction of the user based on physiological data acquired from a user, and communication of the generated fitness data and visual depiction to the user for presentation on a local display device.

FIG. 6 illustrates a method of generating fitness data and a visual depiction of the user based on physiological data acquired from a user, and communication of the generated fitness data to the user for presentation on a local display device. According to this method, physiological data is acquired 602 from the user and transmitted to a network server via a mobile terminal. The physiological data is integrated 604 into the virtual physiological model representative of the user. Fitness data is generated 606 using data associated with the virtual physiological model. A depiction of the user is generated 608 using virtual physiological model data. Changed data or a changing depiction of the user (i.e., avatar) are generated 610 in response to changed virtual physiological model data, prediction analysis or input of test physiological data set(s).

The physiological data and user depictions are communicated 612 to the user via the mobile terminal or other access/display device. Physiological data and user avatar(s) can be displayed 614 on a mobile terminal display, television, WEB terminal, or other use access/display device.

The foregoing description of the various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A method of interacting with a virtual physiological model of a user in the form of an avatar with use of a mobile communication device, comprising:

acquiring physiological data associated with the user, at least some of the physiological data acquired by a sensor configured for sensing a parameter associated with the user's physiology;

transmitting the physiological data to the mobile communication device;

using the mobile communication device to communicate the physiological data to a network server; and integrating the physiological data into the avatar of the user.

2. The method of claim 1, wherein the at least some of the physiological data is acquired using a physiological sensing device in contact with the user.

3. The method of claim 1, wherein acquiring the physiological data comprises inputting at least some of the physiological data using the mobile communication device.

4. The method of claim 1, wherein acquiring the physiological data comprises acquiring heart rate data associated with the user.

5. The method of claim 1, wherein acquiring the physiological data comprises acquiring the user's weight.

6. The method of claim 1, wherein acquiring the physiological data comprises acquiring caloric consumption data associated with the user.

7. The method of claim 1, wherein acquiring the physiological data comprises acquiring a parameter of the user's blood.

8. The method of claim 1, wherein acquiring the physiological data comprises acquiring information concerning the user's diet.

9. The method of claim 1, wherein acquiring the physiological data comprises acquiring anatomical measurements of the user.

10. The method of claim 1, further comprising developing a plurality of physical characteristics of the user using the physiological data of the avatar.

11. The method of claim 10, wherein the plurality of physical characteristics of the user comprises one or more of muscle mass, percent body fat, anatomical dimensions, energy consumption, stress level, heart rate characteristics, and rate of recovery from an exercise regimen.

12. The method of claim 1, further comprising creating at least part of the avatar by the user.

13. The method of claim 12, wherein creating at least part of the avatar comprises defining a plurality of physical or physiological features of the user.

14. A method of interacting with a virtual physiological model of a user in the form of an avatar with use of a mobile communication device, comprising:
    acquiring physiological data associated with the user and transmitting the physiological data to a network server using the mobile communication device, at least some of the physiological data acquired by a sensor configured for sensing a parameter associated with the user's physiology;
    integrating the physiological data into the avatar of the user;
    generating fitness data using physiological data associated with the avatar; and
    communicating the fitness data to the user.

15. The method of claim 14, wherein the fitness data comprises heart rate data associated with a specified period of time.

16. The method of claim 14, wherein the fitness data comprises data associated with a rate at which the user recovers from an exercise regimen.

17. The method of claim 14, wherein the fitness data comprises a mapping of heart rate data to a plurality of states of physiological data or user depictions developed from the virtual physiological model.

18. The method of claim 14, wherein the fitness data comprises stress level data associated with the user.

19. The method of claim 14, wherein the fitness data comprises one or both of percent body fat data and muscle mass of the user.

20. The method of claim 14, wherein communicating the fitness data comprises communicating a plurality of physical characteristics of the user based on the physiological data associated with the avatar.

21. The method of claim 14, wherein communicating the fitness data comprises communicating a depiction of the user based on the physiological data associated with the avatar.

22. The method of claim 21, wherein communicating the depiction of the user comprises depicting changes to the user's depiction in response to changes to the physiological data associated with the virtual physiological model of the user.

23. The method of claim 21, wherein communicating the depiction of the user comprises depicting changes to one or more anatomical dimensions of the user.

24. The method of claim 21, wherein communicating the depiction of the user comprises depicting changes to one or more physical or physiological characteristics of the user in response to changes in a fitness regimen.

25. The method of claim 21, wherein communicating the depiction of the user comprises depicting changes to one or more physical or physiological characteristics of the user in response to changes in the user's diet.

26. The method of claim 21, wherein communicating the depiction of the user comprises communicating one or both of graphical and textual information based on the physiological data associated with the avatar.

27. The method of claim 14, further comprising analyzing historical physiological data of the avatar to predict changes in the fitness data over time.

28. The method of claim 14, further comprising analyzing historical physiological data of the avatar to predict changes in the fitness data in response to a set of input data applied to the avatar.

29. The method of claim 28, wherein the set of input data comprises a set of current physiological data acquired from the user or a set of test physiological data input by the user.

30. The method of claim 14, wherein acquiring the physiological data comprises acquiring heart rate data associated with the user.

31. A mobile physiological information system, comprising:
    a mobile communication device;
    a physiological sensor device adapted for acquiring physiological data associated with the user; and
    a transfer device communicatively coupled to the physiological sensor device and the mobile communication device, the transfer device transmitting the physiological data to the mobile communication device for subsequent integration into a virtual physiological model of the user in the form of an avatar.

32. The system of claim 31, wherein the physiological sensor device comprises a heart rate monitor.

33. The system of claim 31, wherein the physiological sensor device comprises a portable heart rate monitor, the portable heart rate monitor comprising a harness system for providing physical coupling between the physiological sensor device and a portion of the user's anatomy.

34. The system of claim 31, wherein the physiological sensor device comprises one or more of a blood pressure sensor device, an oxygen saturation measuring device, an oxygen consumption measuring device, and a blood chemistry measuring device.

35. The system of claim 31, wherein the physiological sensor device comprises a body fat sensor device.

36. The system of claim 31, wherein the transfer device comprises a short range wireless communication device.

37. The system of claim 31, wherein the physiological sensor device comprises a housing adapted to support the physiologic sensor device on a planar surface, the transfer device disposed in or on the housing.

38. The system of claim 31, wherein the mobile communication device comprises a user interface, the user interface comprising a display and a user input device for facilitating input of user input data for subsequent integration into the avatar.

39. A mobile physiological information system that communicates with a network and a network server, comprising:
- a fitness data engine operable at the network server;
- a mobile communication device;
- a physiological sensor device adapted for acquiring physiological data associated with the user; and
- a transfer device communicatively coupled to the physiological sensor device and the mobile communication device, the transfer device transmitting the physiological data to the mobile communication device, and the mobile communication device communicating the physiological data to the fitness data engine, the fitness data engine integrating the physiological data into a virtual physiological model of the user in the form of an avatar and generating fitness data using physiological data associated with the avatar for subsequent transmission to the user.

40. The system of claim 39, wherein the fitness data engine generates a depiction of the user based on the physiological data associated with the avatar.

41. The system of claim 40, wherein the fitness data engine generates an adjusted depiction of the user in response to new or changed physiological data associated with the avatar.

42. The system of claim 39, wherein the fitness data engine transmits the fitness data to the mobile communication device via the network.

43. The system of claim 39, wherein the fitness data engine transmits the fitness data to a WEB terminal device via the network.

44. The system of claim 39, wherein the fitness data engine transmits the fitness data to a television.

45. The system of claim 39, wherein the physiological sensor device comprises a heart rate monitor.

46. The system of claim 39, wherein the physiological sensor device comprises a portable heart rate monitor, the portable heart rate monitor comprising a harness system for providing physical coupling between the physiological sensor device and a portion of the user's anatomy.

* * * * *